US010528701B2

(12) United States Patent
Heldt et al.

(10) Patent No.: US 10,528,701 B2
(45) Date of Patent: Jan. 7, 2020

(54) SYSTEM AND METHOD FOR SEPSIS CARE TASK MANAGEMENT

(71) Applicants: Massachusetts Institute of Technology, Cambridge, MA (US); The General Hospital Corporation, Boston, MA (US)

(72) Inventors: Thomas Heldt, Cambridge, MA (US); Andrew Tomas Reisner, Newton, MA (US); Michael Filbin, Jamaica Plain, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 526 days.

(21) Appl. No.: 15/045,074

(22) Filed: Feb. 16, 2016

(65) Prior Publication Data
US 2016/0239611 A1 Aug. 18, 2016

Related U.S. Application Data

(60) Provisional application No. 62/117,020, filed on Feb. 17, 2015.

(51) Int. Cl.
*G06F 19/00* (2018.01)
(52) U.S. Cl.
CPC .................. *G06F 19/324* (2013.01)
(58) Field of Classification Search
CPC ... A61B 5/412; A61B 5/7275; G06F 19/3468; G06F 19/325; G06F 19/324; G06F 19/00;
(Continued)

(56) References Cited

U.S. PATENT DOCUMENTS 5,942,986 A 8/1999 Shabot et al.
6,216,032 B1 4/2001 Griffin et al.
(Continued)

FOREIGN PATENT DOCUMENTS

WO WO-2013183001 12/2013

OTHER PUBLICATIONS

International Search Report for PCT/US2016/018118 dated Jun. 17, 2016.
(Continued)

*Primary Examiner* — Maroun P Kanaan
(74) *Attorney, Agent, or Firm* — Wolf, Greenfield & Sacks, P.C.

(57) ABSTRACT

Systems and methods are disclosed for sepsis care management. First data regarding a patient and second data regarding a clinician's treatment of a patient are received by at least one processor. The first data regarding the patient is processed to assess a likelihood that the patient would benefit from administration of each of one or more critical actions for treatment of sepsis, wherein at least one of the one or more critical actions relates to a request for at least one additional diagnostic action. A target treatment protocol, comprising a decision for each of the one or more critical actions, is determined based on the assessed likelihoods. The second data regarding a clinician's treatment of the patient is compared to the target treatment protocol and a notification is provided to the clinician if the second data is incompatible with the target treatment protocol.

33 Claims, 7 Drawing Sheets

(58) Field of Classification Search
CPC ............ G06F 19/3456; G06F 19/3481; G06F 16/2462; G06F 2216/03; A61C 19/06; G16H 40/40; G16H 40/67; G16H 50/20; G16H 50/30; G16H 80/00; G16H 40/63; G16H 10/60; G16H 15/00; G16H 20/10; G16H 10/40; G16H 50/70

See application file for complete search history.

(56) References Cited

U.S. PATENT DOCUMENTS

| | | | |
|---|---|---|---|
| 7,022,070 | B2 | 4/2006 | Ebner et al. |
| 7,758,503 | B2 | 7/2010 | Lynn et al. |
| 7,941,199 | B2 | 5/2011 | Kiani |
| 8,439,835 | B1 | 5/2013 | McKinley et al. |
| 8,527,449 | B2 | 9/2013 | Gajic et al. |
| 8,862,196 | B2 | 10/2014 | Lynn |
| 8,920,318 | B2 | 12/2014 | Inbar |
| 8,922,377 | B2 | 12/2014 | Carnes |
| 8,930,318 | B1 | 1/2015 | Petkov et al. |
| 2007/0255593 | A1 | 11/2007 | Muehlmeier et al. |
| 2009/0149724 | A1 | 6/2009 | Mark et al. |
| 2009/0281839 | A1 | 11/2009 | Lynn et al. |
| 2010/0121170 | A1* | 5/2010 | Rule .................... A61B 5/1427 600/365 |
| 2013/0296720 | A1 | 11/2013 | Mckinley et al. |
| 2014/0005502 | A1 | 1/2014 | Klap et al. |
| 2014/0371543 | A1 | 12/2014 | Steinhauer et al. |
| 2015/0019236 | A1 | 1/2015 | Boyer et al. |
| 2015/0154367 | A1* | 6/2015 | Shetty .................... G06F 19/345 705/2 |
| 2015/0161331 | A1* | 6/2015 | Oleynik .................. G06F 19/00 705/3 |
| 2015/0332012 | A1* | 11/2015 | Edelson ................. G16H 50/30 705/2 |

OTHER PUBLICATIONS

Hans-Joachim Priebe "Protocol-based care for early septic shock," New England Journal of Medicine 371:384-387 (2014).

Herasevich et al., "Designing and testing computer based screening engine for severe sepsis/septic shock," AMIA Annu. Symp. Proc., 6:966 (2008).

Liu et al., "Hospital deaths in patients with sepsis from 2 independent cohorts," JAMA 312(1):90-92 (2014).

The ARISE Investigators and the ANZICS Clinical Trials Group, "Goal-directed resuscitation for patients with early septic shock," New England Journal of Medicine 371:1496-1506 (2014).

Thompson et al., "Sepsis Alert and Diagnostic System. Integrating Clinical Systems to Enhance Study Coordinator Efficiency," CIN 21(1):22-26 (2003).

* cited by examiner

SYSTEM AND METHOD FOR SEPSIS CARE TASK MANAGEMENT

CROSS REFERENCE TO RELATED APPLICATIONS

This application claims the benefit of U.S. Provisional Application No. 62/117,020, filed on Feb. 17, 2015, which is incorporated herein by reference in its entirety. This application is related to PCT Application No. PCT/US2016/018118, filed Feb. 16, 2016, which is hereby incorporated herein by reference in its entirety.

BACKGROUND

Sepsis is a dangerous and common medical emergency. According to The Journal of the American Medical Association, a large United States inpatient sample revealed both that sepsis currently accounts for a remarkable 1 in every 2-3 hospital deaths and that the typical fatality was admitted to the hospital with less severe symptoms before worsening and succumbing to illness. Once severe sepsis has developed, it has a very high mortality rate. Three recent multicenter trials, published in the New England Journal of Medicine, demonstrated that none of the leading strategies for treating septic shock was superior, and none improved mortality to less than 20%. Yet despite this staggeringly high mortality, current medical practice lacks standards about some of the most basic aspects of sepsis care, which puts patients at risk and creates medico-legal risk for the care provider and the hospital. The problem arises because sepsis has an insidious onset. It begins with a more mild form of infection, before it develops into a truly life-threatening illness. In theory, if aggressive treatment were to be initiated and consequently administered when the infection was in its earlier, milder state, then sepsis and critical illness could be either avoided altogether, or at least mitigated. Yet mild infections are exceedingly common, and there is currently no single test or clinical finding that clearly defines the progression of infection and the development of a severe, life-threatening septic state.

The strategies currently employed to combat sepsis leave much to be desired, as sepsis has a high mortality rate and causes a large portion of hospital deaths. In the past, much attention has focused on early sepsis detection. One approach attempts to automatically diagnose sepsis based on vital signs and alert the clinician. However, such an approach does not account for the insidious onset of sepsis and the consequence that the patient's condition evolves over time, while management may lag. Some systems attempt to enforce general clinical orders to avoid lapses, ranging from delayed enactment of initial orders to delayed re-evaluation and delayed ordering of subsequent treatments, but these systems do not yield improved outcomes if the treatment provided is idiosyncratic and not reconsidered frequently.

SUMMARY OF THE INVENTION

Systems and methods are described herein for sepsis care management. First data regarding a patient and second data regarding a clinician's treatment of a patient are received by at least one processor. The first data regarding the patient is processed to assess a likelihood that the patient would benefit from administration of each of one or more critical actions for treatment of sepsis, wherein at least one of the one or more critical actions relates to a request for at least one additional diagnostic action. A target treatment protocol, comprising a decision for each of the one or more critical actions, is determined based on the assessed likelihoods. The second data regarding a clinician's treatment of the patient is compared to the target treatment protocol and a notification is provided to the clinician if the second data is incompatible with the target treatment protocol.

In one implementation, additional data regarding the patient is received at a later time and processed to assess an updated likelihood that the patient would benefit from administration of each of the one or more critical actions for the treatment of sepsis. It is determined whether the updated likelihood is significantly different from the first likelihood, and an updated target treatment protocol for treating the patient is determined based on the updated likelihood.

In one implementation, a second notification is provided to the clinician when the updated likelihood is significantly smaller than the first likelihood, the second notification indicating that at least one of the one or more critical actions previously recommended in the target treatment protocol is not currently recommended in the updated target treatment protocol.

In one implementation, the first data comprises at least one of an age of the patient, a medical history of the patient, a complaint of the patient, and physiological data recorded from the patient.

In one implementation, the second data comprises data recorded by a plurality of devices that communicate information regarding treatment of the patient, and at least one device in the plurality of devices includes at least one of (1) a measurement device that measures an amount of a fluid flowing into or out of the patient, (2) a bar code scanner that scans a label of a medication that is administered to the patient, and (3) a touchscreen monitor that accepts as input data indicative of a medication that is administered to the patient.

In one implementation, processing the first data to assess the risk of sepsis for the patient comprises providing the first data into a statistical probability model that computes the likelihood that the patient would benefit from administration of at least one of the critical actions, wherein the likelihood is computed specifically for the patient.

In one implementation, determining the target treatment protocol comprises comparing the likelihoods to a corresponding set of predetermined thresholds, wherein each of the predetermined thresholds corresponds to one of the plurality of critical actions, and wherein the predetermined thresholds are different for the different critical actions.

In one implementation, determining the target treatment protocol further comprises selecting a set of binary decisions, each binary decision corresponding to one of the plurality of critical actions, wherein the binary decision for each respective critical action is based on whether the respective likelihood exceeds the respective predetermined threshold, wherein the target treatment protocol corresponds to the set of binary decisions.

In one implementation, each candidate treatment protocol in a plurality of candidate treatment protocols comprises a set of binary decisions related to the one or more critical actions, and wherein at least one of the critical actions is related to at least one of the group consisting of diagnostic tests, antibiotics administration, fluid administration, and vasopressor administration.

In one implementation, it is determined whether the second data is incompatible with the target treatment protocol by evaluating a discrepancy between the target treatment protocol and the second data and determining that the discrepancy exceeds a predetermined threshold.

According to another aspect, the disclosure relates to a system to carry out the method described above. In particular, a system is described for sepsis care management. The system comprises at least one input port, at least one processor, and an output port. The at least one input port is configured to receive (1) first data regarding a patient and (2) second data regarding a clinician's management of the patient. The at least one processor that is in communication with the at least one input port and is configured to process the first data to assess a likelihood that the patient would benefit from administration of each of one or more critical actions for treatment of sepsis, wherein at least one of the one or more critical actions relates to a request for at least one additional diagnostic action, determine a target treatment protocol for treating the patient based on the assessed likelihoods, wherein the target treatment protocol comprises a decision for each of the one or more critical actions, and compare the second data to the target treatment protocol. The output port is configured to provide a notification to the clinician if the second data is incompatible with the target treatment protocol.

In one implementation, the at least one input port is further configured to receive, at a second time later than the first time, additional first data regarding the patient. The at least one processor is further configured to process the additional first data to assess an updated likelihood that the patient would benefit from administration of each of the one or more critical actions for the treatment of sepsis, determine whether the updated likelihood is significantly different from the first likelihood, and determine an updated target treatment protocol for treating the patient based on the updated likelihood.

In one implementation, the output port is further configured to provide a second notification to the clinician when the updated likelihood is significantly smaller than the first likelihood, the second notification indicating that at least one of the one or more critical actions previously recommended in the target treatment protocol is not currently recommended in the updated target treatment protocol.

In one implementation, the first data comprises at least one of an age of the patient, a medical history of the patient, a complaint of the patient, and physiological data recorded from the patient.

In one implementation, the second data comprises data recorded by a plurality of devices that communicate information regarding treatment of the patient, and at least one device in the plurality of devices includes at least one of (1) a measurement device that measures an amount of a fluid flowing into or out of the patient, (2) a bar code scanner that scans a label of a medication that is administered to the patient, and (3) a touchscreen monitor that accepts as input data indicative of a medication that is administered to the patient.

In one implementation, the at least one processor is configured to process the first data to assess the likelihood by providing the first data into a statistical probability model that computes the likelihood that the patient would benefit from administration of at least one of the critical actions, wherein the likelihood is computed specifically for the patient.

In one implementation, the at least one processor is configured to determine the target treatment protocol by comparing the likelihoods to a corresponding set of predetermined thresholds, wherein each of the predetermined thresholds corresponds to one of the plurality of critical actions, and wherein the predetermined thresholds are different for the different critical actions.

In one implementation, the at least one processor is configured to determine the target treatment protocol by selecting a set of binary decisions, each binary decision corresponding to one of the plurality of critical actions, wherein the binary decision for each respective critical action is based on whether the respective likelihood exceeds the respective predetermined threshold, wherein the target treatment protocol corresponds to the set of binary decisions.

In one implementation, each candidate treatment protocol in a plurality of candidate treatment protocols comprises a set of binary decisions related to the one or more critical actions, and wherein at least one of the critical actions is related to at least one of the group consisting of diagnostic tests, antibiotics administration, fluid administration, and vasopressor administration.

In one implementation, the at least one processor is further configured to determine whether the second data is incompatible with the target treatment protocol by evaluating a discrepancy between the target treatment protocol and the second data and determining that the discrepancy exceeds a predetermined threshold.

BRIEF DESCRIPTION OF THE DRAWINGS

The system and methods may be better understood from the following illustrative description with references to the following drawings in which.

DETAILED DESCRIPTION

Figure 1:
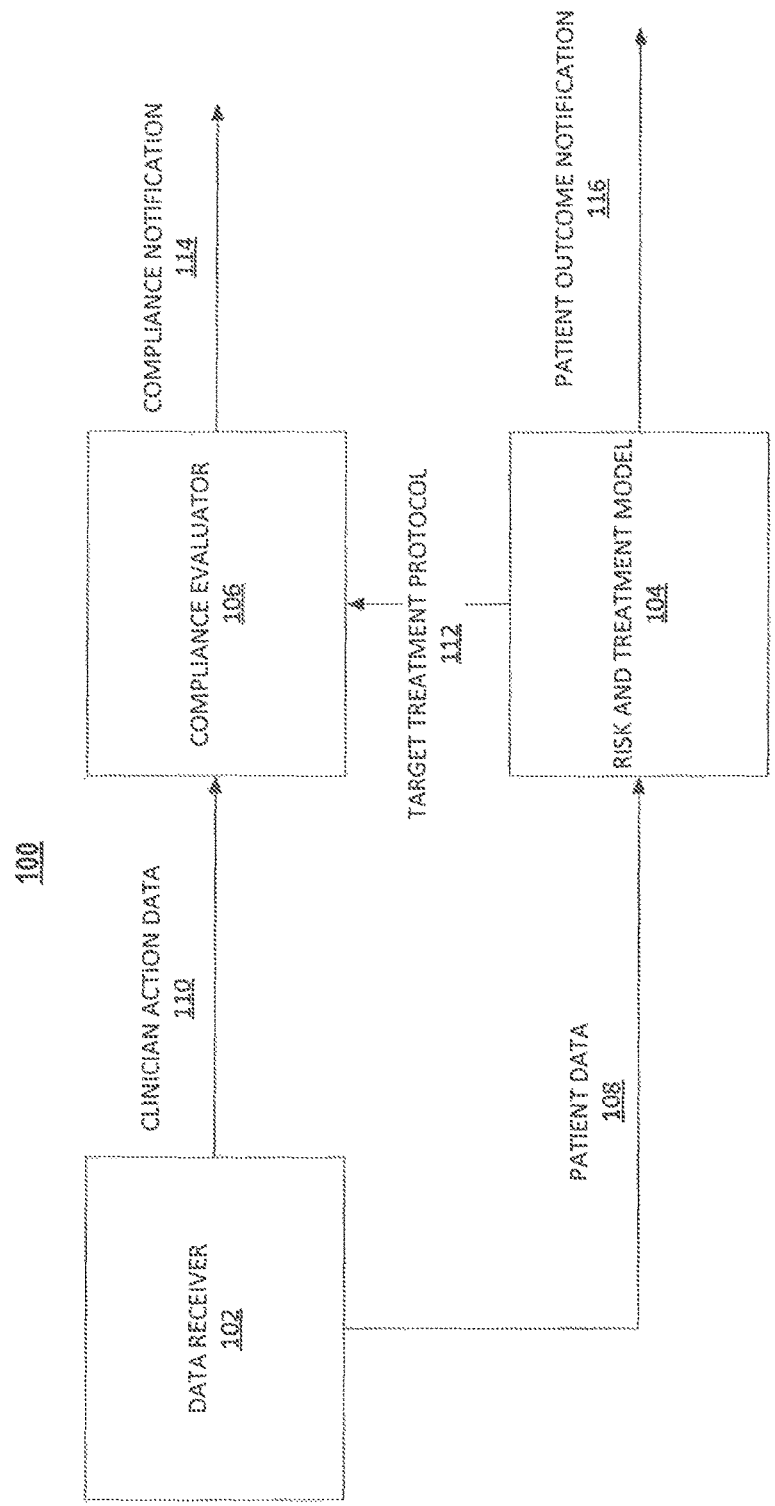
FIG. 1 is a block diagram of a computerized system for sepsis care management, according to an illustrative embodiment.

Much attention has focused in the past on early sepsis detection or on treatment protocols once the patient has been diagnosed with severe sepsis or septic shock. In contrast, very little attention has focused on developing methods and systems for tracking adherence to a sepsis care protocol. The usual assumption is that once a clinician writes the orders for treatment initiation, the orders will be followed consequently and expeditiously, and that staff will also routinely re-assess patients after various interventions, to evaluate treatment efficacy and, when necessary, provide subsequent interventions. Yet in practice, while the patient's condition evolves through time, management may lag, ranging from delayed enactment of initial orders to delayed re-evaluation and delayed ordering of subsequent treatments.

The system and methods of the present disclosure relate to treating potentially septic patients, to efficiently determine which patients have sepsis and to avoid delays in interventions prior to the availability of diagnostic certainty. This reduces treatment delays for the subset of patients who do eventually prove to be septic. The system described herein provides decision support involving a set of "critical actions" for patients with potential sepsis, including both diagnostic and therapeutic actions. Underlying the decision support are computational models that output the probability (based on available data) that each of these critical actions is sufficiently likely to be beneficial to a patient (e.g., are above a pre-set threshold for action). Clinicians often operate without complete diagnostic data. Without complete information, the output probabilities are relatively likely to fall in an "indeterminate" range that does not provide a definitive diagnosis. Nonetheless, for each decision-support decision, the present disclosure uses models that can provide estimates or recommend decisions, even without complete information. As one example, simple "if-then" logic may be used. Although a critical action can still be advised when an indeterminate probability is computed (depending on the configured threshold for action), the indeterminate probability may also trigger the guidance to pursue one or more additional diagnostic actions intended to provide more complete data that allows for the application of a more definitive discriminatory probability model. The systems and methods of the present disclosure guide clinicians to initiate critical actions for patients who might have sepsis, provided that the threshold probability that the critical action is clinically advisable is exceeded. For patients who are later determined to actually have sepsis, this early initiation of treatments even before definitive knowledge should minimize the delays for therapeutic action. Many patients will not ultimately be septic, and the systems and methods of the present disclosure will, after additional diagnostic data are returned, issue decision support that may be equivalent to a "stand down" message indicating that, since the probability that a patient has sepsis or would benefit from a critical action has decreased below the threshold for a given critical action, that critical action(s) is no longer needed. In addition to the aforementioned functionality, the present disclosure also check whether or not the clinician has actually performed the critical actions recommended by the system, and provides guidance related to critical actions that are not being performed.

Described herein are sepsis care management systems and methods that integrate available data relating to the patient and the treatment the patient is receiving to prescribe and enforce standardized sepsis treatment protocols that are continuously monitored and re-evaluated as the patient's condition evolves to provide individualized care within clinical guidelines. To provide an overall understanding, certain illustrative implementations will now be described. However, it will be understood by one of ordinary skill in the art that the systems and methods described herein may be adapted and modified as is appropriate for the application being addressed and may be employed in other suitable applications, and that such other additions and modifications will not depart from the scope thereof.

FIG. 1 depicts a block diagram of a computerized system 100 for sepsis care management, according to some embodiments. The system 100 includes a data receiver 102, a risk and treatment model 104, and a compliance evaluator 106. The data receiver 102 aggregates data related to the patient and communicates it to the risk and treatment model 104 and the compliance evaluator 106. Specifically, the data receiver 102 transmits patient data 108 to the risk and treatment model 104, which determines a risk for sepsis that is specific to the patient. Moreover, the risk and treatment model 104 selects an appropriate target treatment protocol 112 that addresses the patient's specific risk of sepsis. The compliance evaluator 106 receives clinician action data 110 from the data receiver 102 and compares the clinician action data 110 to the target treatment protocol 112. If the clinician action data 110 is incompatible with the target treatment protocol 112, the compliance evaluator 106 determines that the treatment is non-compliant and sends the compliance notification 114 (e.g., as a pager message or over a clinician interface) to alert the clinician.

The data receiver 102 aggregates data from multiple sources. In an example, the data receiver 102 receives data from one or more smart treatment devices, which may include treatment devices capable of communicating the administered treatment to the data receiver 102. For example, a source may include an infusion pump, an IV bag, or a urine bag that measures fluid flowing into and/or out of the patient or a smart ventilator. Additional treatment information, such as antibiotic administration, can be provided by the clinician to the data receiver 102 through an interface, such as a touchscreen, a barcode reader that communicates antibiotic information, or clinical records. This data is aggregated into clinician action data 110 and communicated to the compliance evaluator 106.

Additionally, the data receiver 102 can interface with the patient's physiological monitors in order to receive real time physiological data such as an EKG, respiration rate, blood pressure, and oxygen saturation. The data receiver 102 can also interface with the hospital records system to retrieve patient data such as medical history, the patient's chief complaints, lab test results, and radiological data. This data is aggregated into patient data 108 and communicated to the risk and treatment model 104. The data receiver 102 is described in more detail in relation to FIG. 2.

The risk and treatment model 104 determines if the patient is at risk for sepsis and the target treatment protocol 112. A statistical probability model takes the patient data 108 as input and generates an indicator of the specific risk to the patient posed by sepsis. This risk indicator, which can be displayed to the clinician, is then used to select an appropriate target treatment protocol 112 from a set of candidate treatment protocols, each of which prescribe specific intended clinical actions for a range of sepsis risks. For example, the intended clinical actions may include diagnostic tests, antibiotics administration, fluid administration, and vasopressor administration, that should be conducted during a prescribed time-duration.

In some implementations, the risk and treatment model 104 tracks the historical trajectory of the patient's status and/or the recent history of the patient's risk of sepsis and patient data 108. When the historical trajectory data reveals a significant improvement, deterioration, or adverse effect in the patient's status or health condition, the risk and treatment model 104 may use patient outcome notification 116 to notify the clinician that the target treatment protocol 112 may need to be re-evaluated. In some implementations, the clinician action data 110 is also made available to the risk and treatment model 104 to be included in trajectory calculations. As an example, logical operations on the measurement(s) from a smart IV device may reveal a risk for congestive heart failure. The risk and treatment model 104 is described in more detail in relation to FIG. 3.

The compliance evaluator 106 evaluates whether the treatment administered to the patient complies with the target treatment protocol 112. As described above, the clinician action data 110 can include data provided by any number of smart treatment devices, clinician input and records, or both. This data is compared to the target treatment protocol 112 to determine whether both the treatments administered and the timing of the administration adhere to the target treatment protocol 112. Any discrepancies that are considered significant, for example discrepancies that vary by more than a threshold amount, may be reported to the clinician using compliance notification 114. In an example, the threshold amounts that are used to determine whether any discrepancies are significant may be set by a user, who may be a hospital administrator, hospital compliance officer, or any person who is authorized to configure the systems and methods of the disclosure. In general, the compliance notification 114 and/or the patient outcome notification 116 may be transmitted to one or more members of the clinical staff via pager message, on-screen alert, text message, e-mail, or a message transmitted to the emergency medical records (EMR). The compliance evaluator 106 is described in more detail in relation to FIG. 4.

The system and methods of the present disclosure allow for continuous monitoring of potentially septic patients that evolves with the patients' conditions. Clinicians can set standards for initiating treatment, which can begin before diagnostic tests are completed and while sepsis remains in its mild onset stage, since the risk and treatment model 104 can provide preliminary assessments with minimal and incomplete data. In some implementations, the data receiver 102 continuously receives new information (e.g., the ordering of diagnostic tests and the patient's physiological response to treatment) as it becomes available to provide the risk and treatment model 104 with updates that enable refined treatment decisions that take into account this new information. The compliance evaluator 106 determines whether the updated instructions are followed and provides a notification to the clinician when the clinician's actions differ from the updated instructions.

As used herein, the terms "processor", "CPU", or "computing device" refer to one or more computers, microprocessors, logic devices, servers, or other devices configured with hardware, firmware, and software to carry out one or more of the computerized techniques described herein. Processors and processing devices may also include one or more memory devices for storing inputs, outputs, and data that are currently being processed. An illustrative computing device 500, which may be used to implement any of the processors and servers described herein, is described in detail below with reference to FIG. 5.

Figure 2:
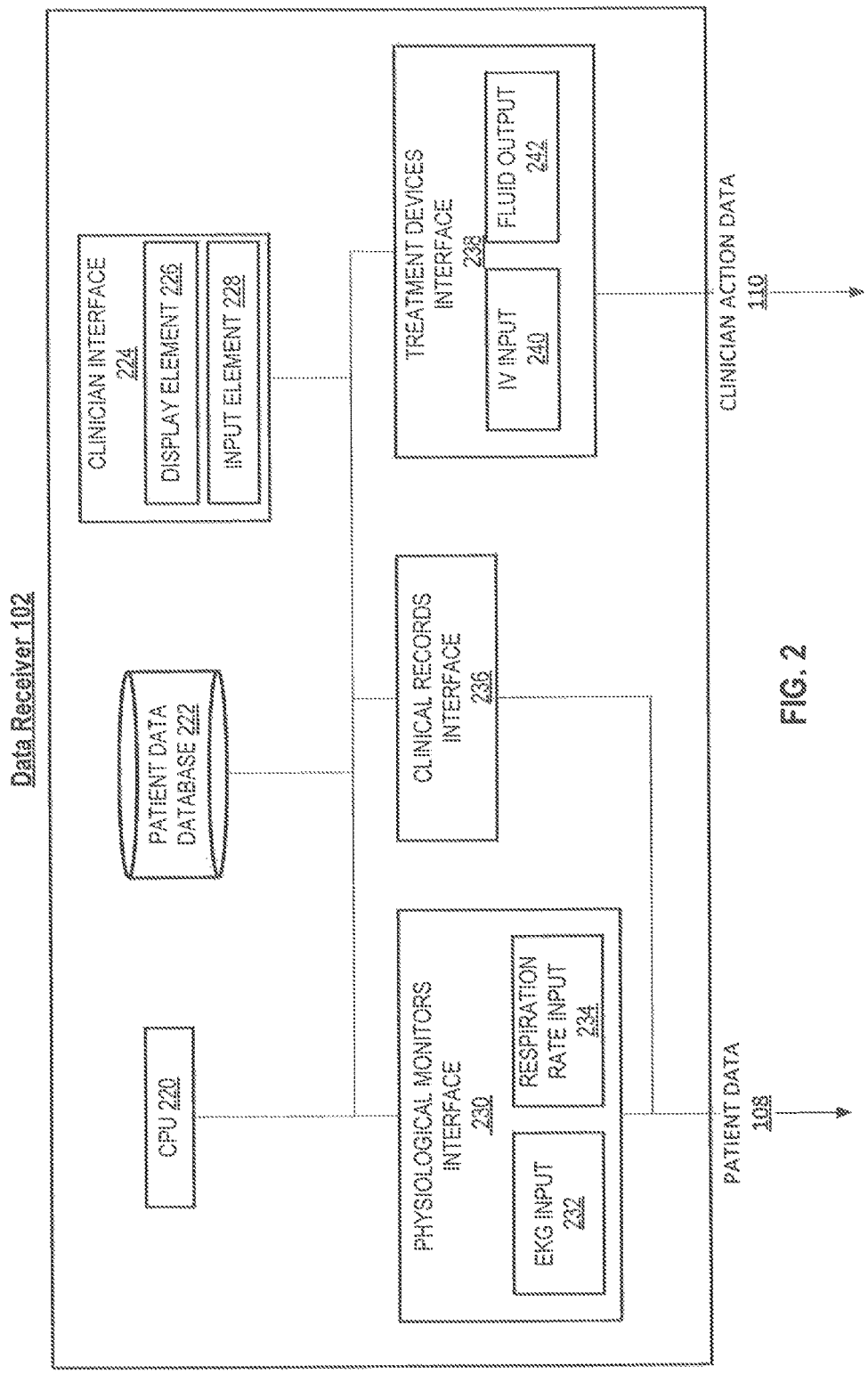
FIG. 2 is a block diagram of a patient data receiver that is used to aggregate patient data, according to an illustrative embodiment.

FIG. 2 depicts a detailed block diagram of the data receiver 102, according to some embodiments. As is shown in FIG. 2, the data receiver 102 includes CPU 220, a patient data database 222, a clinician interface 224 that includes a display element 226 and an input element 228, a physiological monitors interface 230 that includes an EKG input 232 and a respiration rate input 234, a clinical records interface 236, and a treatment devices interface 238 that includes IV input 240 and fluid output 242. The physiological monitors interface 230 is an interface for obtaining real time physiological data from a patient's physiological monitors. EKG input 232 and respiration rate input 234 are shown as two exemplary inputs for electrocardiogram and respiration rate data respectively. In some implementations, inputs for additional monitor data, such as capnography, will be included. The clinical records interface 236 is an interface that obtains clinical information and records, such as lab results, radiological data, and electronic medical records. The treatment devices interface 238 communicates with smart treatment devices, such as the IV input 240 that measures intravenous fluid administration and fluid output 242 that measures the volume of urine produced by the patient. In some implementations, IV input 240 and fluid output 242 are both implemented by attaching strain gauges to the necessary fluid bags in order to use changes in the weight of the fluid bags to characterize the fluid flow. Other implementations may use flow meters or other sensors to assess the flow rate from fluid bags.

Clinician interface 224 is an interface for communication with the clinician. The display element 226 can display, to the clinician, patient information and outputs from the system, such as a sepsis risk indication or the steps of the treatment protocol. Clinician interface 224 also contains the input element 228, through which a clinician can input information, such as antibiotic administration. In some implementations, the clinician interface can be a touch-screen device, a web interface, a combination of a computer monitor and input devices such as a keyboard and/or mouse, or any suitable display element and input device. The information collected through the various interfaces, the physiological monitors interface 230, the clinical records interface 236, the treatment devices interface 238, and the clinician interface 224, is stored in the patient data database 222, operated on and amalgamated by CPU 220, and is communicated to other elements of the present disclosure as patient data 108 and clinician action data 110.

In some implementations, data can be preprocessed before it is communicated to other elements of the invention. Preprocessing may include sampling the physiological data, performing waveform transformations, for example assessment of the signal quality, or any mathematical operation that makes the physiological data suitable for input into the risk and treatment model 104. In some implementations, patient data 108 and clinician action data 110 may be continuously streamed to other elements of the invention in real time, may be made available in whole or in part in response to queries from other elements of the invention, or may be otherwise communicated in any suitable manner.

In some implementations, physiological monitors interface 230 and treatment devices interface 238 includes inputs for video monitoring and/or bar code readers (not shown). Inputs to the physiological monitors interface 230 and treatment devices interface 238 may be configured to accept data from a predetermined type of monitoring device and, possibly, in a predetermined format. In some implementations, the physiological monitors interface 230, the clinical records interface 236, the treatment devices interface 238, and the clinician interface 224, also include general purpose inputs. Such inputs could be configurable by a user to accept data of the user's choosing. Interface inputs can be made over a variety of connections including Ethernet, Bluetooth, and the Institute of Electrical and Electronics Engineers' (IEEE) 802.11 standard.

Figure 3:
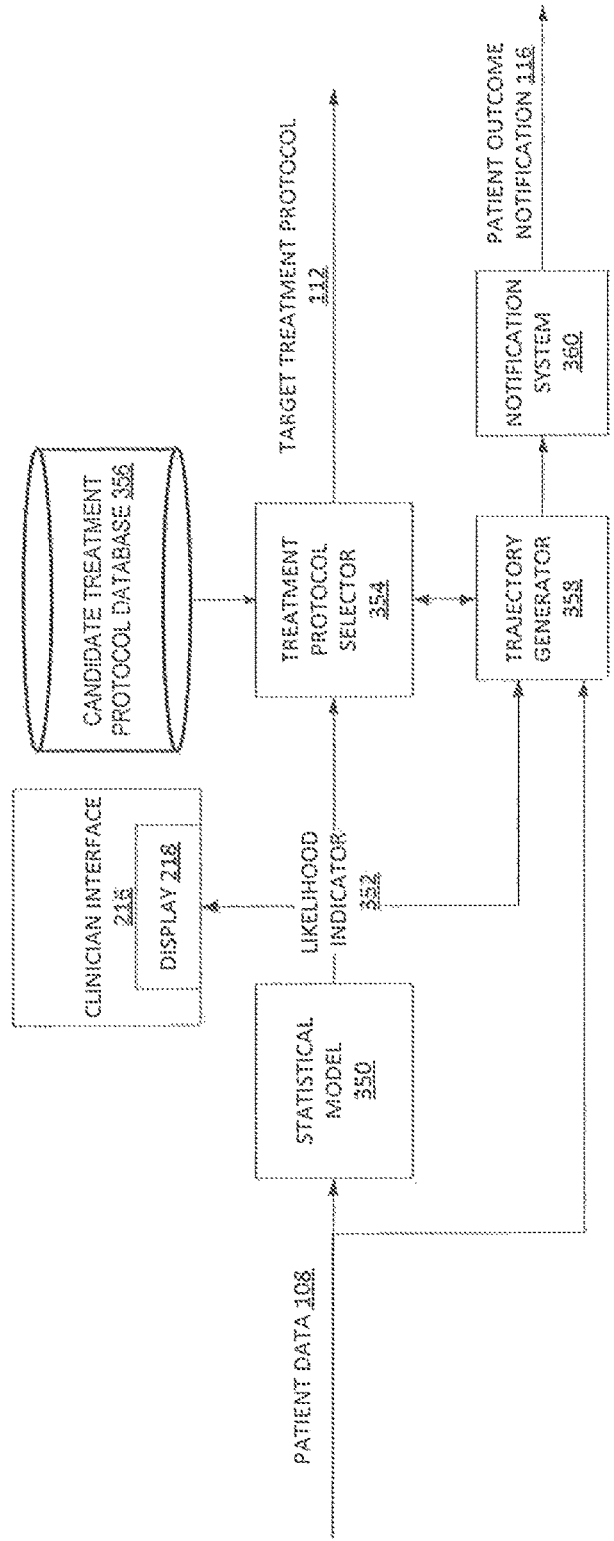
FIG. 3 is a block diagram of a risk and treatment model that is used to assess the risk to the patient posed by sepsis and a corresponding treatment protocol, according to an illustrative embodiment.

FIG. 3 depicts a detailed block diagram of a risk and treatment model 104, according to some embodiments. Patient data 108 is input to statistical model 350, which analyzes the real-time and static data elements, using logistic regression, to calculate the patient's overall likelihood of sepsis. In some implementations, the statistical model 350 can include any model, machine learning classifier, with or without voting strategies, or formula that is selected or input by a user, such as linear regression, support vector machines, and nearest neighbor algorithms. In some implementations, the statistical model 350 incorporates additional data, such as clinician action data 110. In some implementations, the statistical model 350 computes the likelihood that a specific empiric treatment or critical action (e.g., actions that the clinician deems critical to or appropriate for treating sepsis) will be beneficial. Critical actions can include the initiation of a bolus or drip of fluids, a single dose or continued administration of antibiotics, a single or repeated blood pressure measurement, placement of an arterial line, discontinuation of an arterial line, a single bolus or drip of vasopressors, and any other suitable treatment or intervention. Critical actions may include one time actions (or administrations), continuous actions (such as a continuous flow of IV fluid), periodic actions (such as a dose of antibiotics every 6 hours), or any suitable combination thereof. In one example, the statistical model 350 may compute that a patient has a high probability of benefiting from antibiotics based on a subset of the information that would be required to render an accurate sepsis diagnosis. As used herein, the term "empiric treatment" refers to a treatment that is initiated on the basis of limited patient information that is insufficient to render a complete diagnosis with certainty. In one example, an empiric treatment may be administered in the absence of the results of a diagnostic test.

In some implementations, the statistical model 350 incorporates received data into five categories of predictor variables. One such category is physiological measurements, which incorporates physiological monitor data such as blood pressure, heart rate, temperature, pulse oximetry, and respiratory rate measurements, as well as variables based on the patterns of those measurements, including rates of change and variability over a time window, and, finally, metrics related to the shape of the measured physiological waveforms that underlie heart rate, respiratory rate, and oxygen saturation (electrocardiography, pneumography, and photoplethysmography respectively) over a time window. In one implementation, the statistical model 350 compares the current physiological measurements with those documented in prior patient encounters to determine whether the current physiological measurements are typical for that patient. Another category of predictor variable is past medical history variables, which include demographic data, such as age, and quantify whether a patient has a particular pre-existing condition and quantifies the state or extent of conditions. Relevant pre-existing conditions include, for example, active immunosuppressive therapy, active cancer chemotherapy or metastatic disease, long-term institutionalization, or chronic organ dysfunction, especially dysfunction severe enough to cause functional impairment or laboratory test abnormality, e.g. chronic hemodialysis due to renal insufficiency or home oxygen use or chronic hypoxia due to pulmonary disease. A third category of predictor variable is current complaint variables, which quantify whether or not a patient has a particular new clinical complaint, symptom, or symptom complex, such as fevers, chills, night sweats, dysuria, polyuria, abdominal pin, cough, shortness of breath, rash, generalized weakness, fatigue, malaise, "not feeling right", mental status changes/confusion, diarrhea, sore throat, or pus draining from an area. A fourth category of predictor variable is diagnostic data, which quantifies new information related to the patient's current state. Relevant diagnostic data may include a white blood cell count and differential, imaging results like a chest xray or abdominal CT scan that may indicate the presence or absence of an infection like pneumonia or appendicitis, urinalysis that indicates the presence or absence of pyuria, bacteria, or nitrites, and other biomarkers and inflammatory metrics such as erythrocyte sedimentation rate, c-reactive protein, procalcitonin, and blood cultures. A fifth category of predictive variables is management data quantifying the actions and responses of the clinical team, i.e. data related to the presence or absence, the timing, and the quantity of specific therapies, such as intravenous fluids, antibiotics, antipyretics, vasopressors, and endotracheal intubation. Additionally, this category may include parameters relevant to the patient's length of stay, the patient's location in the emergency department or hospital, and whether a surgical intervention was performed, such as an appendectomy, abscess drainage, or ureteral stent placed.

The statistical model 350 represents input data from each category in a suitable format, such as a Boolean, indicator variable, scalar, integer, real number, or imaginary number, or any suitable combination thereof. In some implementations, the inputs are normalized to remove the effect of differing measurement scales. The statistical model 350 incorporates different combinations of input parameters using various feature vectors and weights pre-determined by training a logistical regression or machine learning classifier on training datasets, which can be used to create models that calculate a likelihood of being in a certain state, such as having a 70% chance of being septic or a 30% chance of requiring antibiotic therapy. In some implementations, the weights applied to different parameters of the feature vector are different for different institutions to reflect differences that are present in local patient populations. For example, some tertiary care hospitals have a very sick, frail population of cancer patients. In those institutions, history of active cancer will be a high weight (i.e., high-risk) predictor variable. By contrast, cancer patients who are receiving care at community hospital (rather than a tertiary care hospital) might be (hypothetically) healthier and less frail. Accordingly, the associated risk due to active cancer for patients treated at that community hospital may be reduced on a statistical basis. In some implementations, the elderly patient population might be generally healthier in one institution, whereas in another institution, the elderly population might be generally more debilitated with chronic illness. Accordingly, the weighting of the predictor parameters can be different to produce an optimal predictive performance for the typical patient population of a particular institution. The statistical model 350 transmits the calculated risk (in the form of likelihood indicator 352) to the display 218 on the clinician interface 216, the treatment protocol selector 354, and the trajectory generator 358.

The treatment protocol selector 354 selects a target treatment protocol 112 from a set of candidate treatment protocols, which are stored in the candidate treatment protocol database 356. In particular, the target treatment protocol 112 may be selected by comparing the likelihood indicator 352 to a threshold level of risk. When the likelihood indicator 352 indicates that the patient's sepsis risk is high, i.e. exceeds the threshold, the systems and methods of the present disclosure provide specific protocol support for several interventions, such as antibiotics administration, fluid administration, vasopressor administration, and diagnostic tests. All patients, including those with likelihood indicators 352 indicating a low sepsis risk, may be monitored and reevaluated on an ongoing basis, so that the patient's specific risk of sepsis is updated periodically to reflect the patient's latest data. When likelihood indicator 352 is "non-diagnostic," i.e. substantially far from zero and 100% without exceeding the threshold, the systems and methods of the present disclosure may suggest obtaining additional data to yield a better diagnosis.

In some implementations, the treatment protocol selector 354 uses multiple risk thresholds and prescribes distinct interventions for patients whose risk indicator falls between adjacent thresholds. In some implementations, the likelihood indicator 352 is considered along with other factors, such as age, medical history, and chief complaint, or the statistical model 350 considers these other factors when calculating the likelihood indicator 352, such that the likelihood indicator 352 inherently includes such factors. In some implementations, the treatment protocol selector 354 is configurable to use different criteria and different thresholds to advise specific actions and interventions. For example, patients whose likelihood of sepsis exceeds the minimal risk-threshold may receive different treatment if they exceed an age threshold, if their medical records meet a certain criteria, such as listing a condition associated with a heightened risk of congestive heart failure, or if the patient presented with a complaint, such as confusion, that is likely to be related to sepsis. In some implementations, this functionality is based on simple "if-then" statements. A hypothetical example of such an "if-then" functionality may include the following statement: "if likelihood indicator 352 is at least 50% and the physiological and records data 110 reveals the patient has a blood pressure with mean pressure <80 mmHg for at least 45 min", then the system would advise the initiation of vasopressors.

In some implementations, the treatment protocol selector 354 uses a variety of decision models that incorporate different parameters in order to provide increasing discriminatory ability, as indicated, for example, by the receiver operating characteristic curve area under curve (ROC AUC). The discriminatory ability of a model may refer to the ability of the model to provide "definitive" probabilities, and predictive models that have greater amounts of information as inputs (in terms of predictor variable inputs) are often able to yield more definitive decision-making. As an example, model "A" is given, as an input, the patient's age and the patient's triage temperature. If properly developed, model "A" would indeed yield an accurate probability of sepsis (0-100%) based on the input information. However, model "A" would often provide a non-definitive probability, e.g., "55%" or "25%". As another example, model "B" is given all of the different predictor variables described above as inputs. In this example, model "B" also outputs an accurate probability of sepsis (0-100%) based on the input information. More importantly, model "B"'s output would typically be more definitive, e.g. "99.8%" or "0.03%". In other words, when given superior information as a basis for computing a probability, the predictive model can do a better job of functionally outputting a clear, unambiguous classification of the patient.

The treatment protocol selector 354 uses multiple "tiers" of predictive statistical models, with increasing ROC AUCs, that require additional information. The risk and treatment model 104 may survey all available predictor variable information and apply the most discriminatory model to yield a probability that sepsis is present or that an intervention, such as antibiotics or intravascular fluids, is indicated. If the output probability were non-diagnostic, then the system advises additional diagnostic data. For instance, if the treatment protocol selector 354 is configured to advise empiric antibiotics when there is at least a 75% probability that antibiotics were truly necessary and the calculated probability is only 50% based on a simple low-tier statistical model that employed only age and triage temperature as inputs, then the system may advise obtaining additional diagnostic data that would allow for the computation of a more discriminatory model. In some implementations, the treatment protocol selector 354 may be configured to advise empiric therapies. For example, the statistical model 350 and treatment protocol selector 354 may generate predictions that are non-diagnostic but sufficient to indicate that the patient would likely benefit from a specific clinical intervention, such as antibiotics. Empiric therapy may be controlled by configuring distinct thresholds for each tier of model used by the treatment protocol selector 354. The treatment protocol selector 354 may remove critical actions from the target treatment protocol 112 (by implementing a "stand down" instruction related to a specific action). Issuance of a standing down instruction (e.g., temporarily or indefinitely recommending the discontinuing of a critical action) may be appropriate if ongoing surveillance or new diagnostic data indicate that the patient has responded sufficiently well to a previously initiated critical action that is no longer sufficiently likely to be beneficial. For example, a patient who is simply dehydrated would benefit from fluid administration and the likelihood indicator 352 would indicate this with sufficient certainty. The treatment protocol selector 354 would then advise IV fluid administration. Since the patient is only dehydrated (and not septic), the patient's condition would improve rapidly, causing the likelihood indicator 352 to consequently fall below the threshold. This in turn causes the treatment protocol selector 354 to issue a stand down instruction to update the target treatment protocol 112 to remove intravenous fluid administration as a recommended critical action. Standing down may also be appropriate when additional diagnostic tests (and/or the benefit likelihoods calculated therefrom) suggest a target treatment protocol 112 that differs from a previous target treatment protocol 112. A temporary stand down may be issued to discontinue an action for a specified period of time, after which the target treatment protocol 112 may include a recommendation to check on the patient's status or to obtain additional diagnostic data.

In some implementations, the statistical model 350 computes the likelihood that a specific empiric treatment or critical action (e.g., actions the clinician deems critical to or appropriate for treating sepsis), will be beneficial. In one example, the statistical model 350 computes that a patient has a high probability of benefiting from antibiotics based on a subset of the information that would be required to render an accurate sepsis diagnosis. This likelihood (in the form of likelihood indicator 352, for example) is communicated to the treatment protocol selector 354, where the likelihood is compared to a threshold value or provided as input into a decision model to determine whether the treatment should be undertaken. In some implementations, the likelihood indicator is a vector, list, or other suitable data structure, containing a likelihood value for each clinical action. In other implementations, each potential treatment method is assigned to a treatment-specific statistical model and treatment protocol selector that only process and provide data related to their respective treatment method. In other implementations, a single model may be configured to render decisions for all of the potential treatment methods by operating iteratively over the possible treatment methods. One of ordinary skill in the art will understand that any suitable statistical model may be implemented without departing from the scope of the present disclosure.

In some implementations, the treatment protocol selector 354 receives a first input vector of likelihoods, where each likelihood in the vector corresponds to a likelihood that a specific patient will benefit from a particular clinical action. Example categories of critical actions may include administration of antibiotics, administration of fluids, administration of vasopressors, the ordering of a particular diagnostic test, or any suitable combination thereof. There may be multiple critical actions for each of these example categories, such as critical actions that specify the type of antibiotic (or fluid or vasopressor) and the dosage amount, or critical actions that specify the particular diagnostic test. The treatment protocol selector 354 also receives a second input vector containing threshold values, where each threshold value corresponds to a threshold likelihood value for each critical action in the first input vector of likelihoods. Importantly, the threshold values in the second input vector correspond to various critical actions and may be set independently from one another.

The first input vector of likelihoods and the second input vector of thresholds are compared to render an output vector of binary decisions indicating whether to initiate each specific critical action. The output vector of binary decisions (which may be referred to herein as positive or negative) provides indications of whether to initiate certain critical actions. When the treatment protocol selector 354 determines that the likely benefit of a critical action (that may have been previously performed or previously recommended to be performed) has decreased below a threshold, or if results show that the patient's condition has actually improved, then a "stand down" instruction may be issued. This may be done by removing the critical action from target treatment protocol 112 by setting the corresponding binary decision to negative, indicating that the specific critical action is not recommended in the target treatment protocol 112.

In some implementations, the above-described first and second input vectors and output vector have variable lengths and include indications as to which critical actions are included, a key value store matching treatment to decision, or some other suitable data structure. In this case, a critical action may be deleted from the structure when it is no longer necessary or recommended in the target treatment protocol 112. In some implementations, the patient outcome notification 116 is sent to the clinician to indicate a stand-down recommendation has been made and treatment using that particular critical action should be halted. The compliance evaluator 106 can also verify whether a stand down instruction was implemented by storing the status, such as active or cancelled, along with orders. When the clinical action data matches a cancelled order, the system can issue compliance notification 114 to alert the clinician that a stand-down instruction was not complied with. In some implementations, compliance notifications regarding cancelled treatments are prompts that allow the clinician to acknowledge the stand down instruction and/or certify that the treatment that was undertaken is unrelated to sepsis.

The candidate treatment protocol database 356 stores a set of candidate treatment protocols, which include a variety of interventions or clinical actions that should be conducted either throughout a prescribed time-duration or within a prescribed time-duration. Four exemplary clinical actions are diagnostic tests, vasopressor administration, IV fluid administration, and antibiotics administration, each of which is described in detail below.

One example of a clinical action is diagnostic testing. Timely diagnostic testing is often required for sepsis management. The systems and methods of the present disclosure provide the diagnostic data necessary for optimal decision-making. In some implementations, sepsis screening is offered on the basis of minimal data such as abnormal heart rate, blood pressure, and respiratory rate, prior to the availability of additional diagnostic data. In some implementations, the present disclosure interfaces with the EMR system to ascertain whether or not development of sepsis was a possibility based on the available patient data (e.g., ascertain whether or not the patient presented to the ER with confusion, which may indicate sepsis, or after a gun shot wound, which is not likely to indicate sepsis). Based on sensitive but non-specific criteria, e.g. patient data that is unlikely to lead to false-negative conclusions but that may lead to an arbitrary rate of false positives, the present disclosure prompts the clinician to order the diagnostic tests necessary to rule-in a bacterial infection. One example of diagnostic data that may be requested, either directly through a hospital interface or through a prompting of the clinician, by the treatment protocol selector 354 includes serum lactates both upon initial evaluation of a patient with potential sepsis and continuously throughout the management of the septic patient, based on the configurable clinical rules selected by the user. In one example, a configurable clinical rule refers to the configuration of candidate treatment protocols or potential critical actions that can be used by the risk and treatment model 104 to offer refined diagnoses. Alternatively or additionally, a configurable clinical rule may refer to the configuration of the likelihood threshold in the second input vector of threshold values described above. Another example of diagnostic data that may be requested by the treatment protocol selector 354 includes a serum natriuretic peptide assay to evaluate patients with reduced oxygen saturation levels for excessive intravascular fluid volumes that make additional intravenous fluids deleterious. In some implementations, the conduct of diagnostic tests is determined by an automated query of the electronic medical records (EMR) or by a direct query of the clinician by the compliance evaluator 106 and clinician interface 224.

Another example of a clinical action involves administration of vasopressors. In some implementations, the treatment protocol selector 354 advises when vasopressors should be initiated, up-titrated, down-titrated, continued, or discontinued. Some implementations of the treatment protocol selector 354 advise when IV fluids should be initiated, bolused, continued, when IV fluids should be held, and when the patient received excessive IV fluids, which is known as congestive heart failure. In some implementations, this is determined by strain gauges for the IV fluid bags, which can measure the mass of the fluids that leaves the bag and infuses into the patient, and transmitted to IV input 240.

Another example of a clinical action involves administration of one or more antibiotics. In some implementations, the treatment protocol selector 354 advises when antibiotics should be initiated, either as a single dose or as periodic doses, continued, or discontinued. The treatment protocol selector 354 can be configured by a user so that the criteria for initiating antibiotics are not the same as the criteria for continuing antibiotics, so that therapy can be initiated even before there are comprehensive diagnostic data available. The clinical formula and threshold for these decisions can be adjusted by the user. In some implementations, the treatment protocol selector 354 also includes statistical models and conditional prompts/logic to help users select optimal antibiotics through messages that may be automatically adjusted based on the clinical information of the specific patient. In some implementations, the statistical model 350 computes separate likelihood indicators for various antibiotics and the treatment protocol selector chooses which antibiotics are recommended for administration, while using logical operations to ensure there are no deleterious interactions between previously administered antibiotics or resultant from existing medical conditions, such as allergies. In some implementations, the clinician is shown, for example over the clinician interface 216, the likelihood that each of several potential antibiotics will be beneficial and can select which to administer. In some implementations, the trajectory generator 358 checks for possible drug interactions using logical operations on the elected treatments, medical records from patient data 108, and configurable drug interaction guidelines. In some implementations, the compliance evaluator 106 determines, based on data provided over the clinician interface 224, when the antibiotics have been initiated, and the compliance evaluator 106 issues a notification to the clinician when antibiotics are not initiated as per the pre-designated time frame.

As is shown in FIG. 3, the likelihood indicator 352 and patient data 108 are provided to the trajectory generator 358, which buffers the input information in order to track the trajectory of the patient's condition and status, for example by computing a difference between each successive likelihood indicator 352. Analysis of the information can reveal the presence of a significant improvement, deterioration, or adverse effect that may warrant reconsideration of the target treatment protocol 112. In some implementations, a user can set thresholds for detected changes, positive or negative, in sepsis likelihood indication and associated time durations, such that the clinician would be notified if the likelihood indication changes by more than the specified amount within a specified time duration, such as a 10% change in less than 30 minutes or a 50% change over 6 hours, or any other suitable amount of change in a specified amount of time. In some implementations, clinician action data 110 is made available to the risk and treatment model 104 to be included in trajectory calculations. For example logical operations on the historical measurement of treatment from a smart IV device could reveal a risk for congestive heart failure. In some implementations, the treatment protocol selector 354 includes models to characterize a patient's response to a previously selected and administered treatment (e.g. a trajectory for the blood pressure of a patient given vasopressors) and can trigger the communication of a patient outcome notification 116 according to configurable guidelines. One example of such a configurable guideline may include a threshold indicating when a difference between the response and the statistical expectation becomes statistically significant.

If a significant improvement, a significant deterioration, or an adverse effect are determined to warrant reconsideration of the treatment, notification system 360 sends patient outcome notification 116 to the clinician to alert the clinician of the determination. In some implementations, the notification system 360 includes pager message, on-screen alert, text message, e-mail, a dedicated display at the patient's bedside, a dedicated screen at a central clinician work area, a dedicated screen or window in the in the workstation used by clinicians for computing tasks, and interface with the clinical information system (CIS), a message transmitted to the EMR, or any suitable combination thereof. In some implementations, the specific language of the notifications can be configured by the user, which allows for some facilities to advise more clinician discretion and other facilities to advise more strict protocol-based responses.

Figure 4:
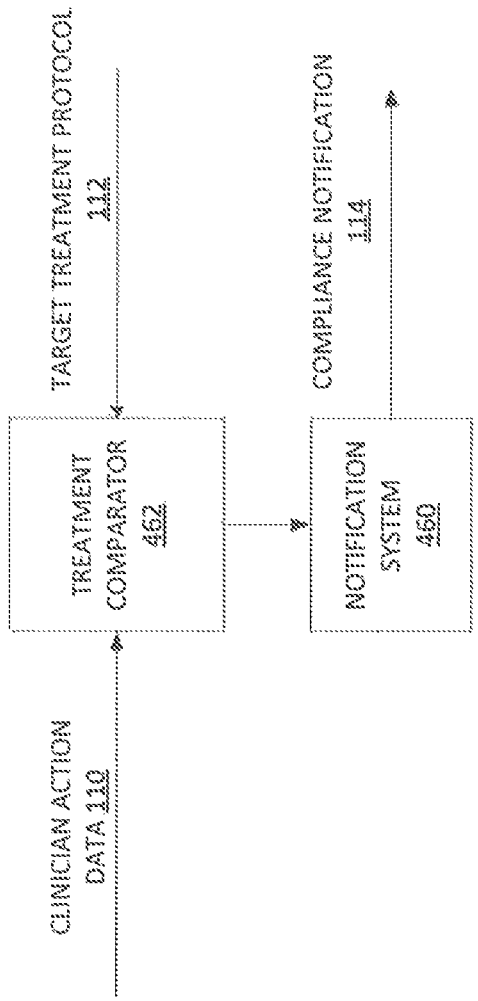
FIG. 4 is a block diagram of a compliance evaluator that is used to evaluate whether the treatment being administered to the patient is in compliance with the treatment protocol, according to an illustrative embodiment.

FIG. 4 depicts a detailed block diagram of a compliance evaluator 106, according to some embodiments. The compliance evaluator 106 evaluates whether the treatment that is actually administered to the patient is compatible with the target treatment protocol 112. Specifically, a treatment comparator 462 determines whether the actual treatment (as indicated by the clinician action data 110) is similar to the recommended treatment (as indicated by the target treatment protocol 112). In particular, the compliance evaluator 106 determines whether the prescribed clinical actions are administered at the proper times. As described above, the clinician action data 110 can be from smart treatment devices as well as clinician input and records. These sources can be identified by the data receiver 102, which can also record the timings of the treatments. Given the treatment and timing, the treatment comparator 462 can apply simple lookup and logical operations to determine compliance. In an exemplary implementation, treatment protocols can be represented as lists of clinical actions, which may include structures that contain at least the type of action, start time, and end time. Using these structures, the treatment comparator 462 parses the list to check if any prescribed treatments in the list have expired, such as if a treatment was not administered prior to its end time. The treatment comparator 462 may check whether incoming treatment data is part of the sepsis treatment protocol, and remove completed treatments from the list, once logical operations on clinician action data 110 indicate the treatment was completed. The treatment comparator 462 allows the user, such as a hospital administrator, hospital compliance officer, or any person who is authorized to configure the systems and methods of the disclosure, to configure the sensitivity of the comparisons such that only the discrepancies that exceed a configurable threshold amount, for example a 1% discrepancy in prescribed and measured IV fluid flow rates, are considered significant. Any significant discrepancies can be reported to the clinician by notification system 360 with compliance notification 114, which is substantially similar to patient outcome notification 116 except for non-compliance related substance of the message.

Figure 5:
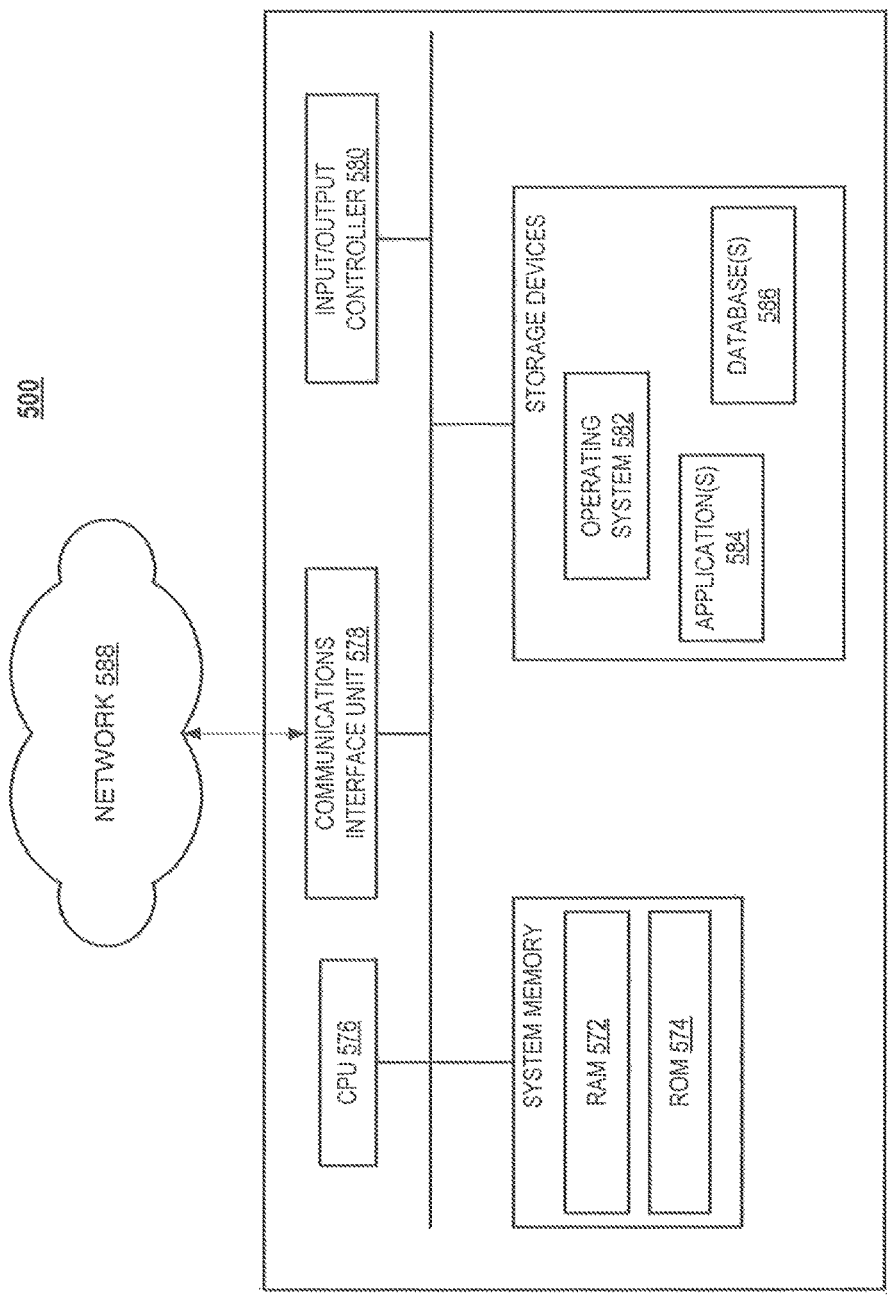
FIG. 5 is a block diagram of an illustrative computing device.

FIG. 5 is a block diagram of a computing device, such as any of the components of the systems of FIG. 1, for performing any of the processes described herein. Each of the components of these systems may be implemented on one or more computing devices 500. In certain aspects, a plurality of the components of these systems may be included within one computing device 500. In certain implementations, a component and a storage device may be implemented across several computing devices 500.

The computing device 500 comprises at least one communications interface unit, an input/output controller 580, system memory, and one or more data storage devices. The system memory includes at least one random access memory (RAM 572) and at least one read-only memory (ROM 574). All of these elements are in communication with a central processing unit (CPU 576) to facilitate the operation of the computing device 500. The computing device 500 may be configured in many different ways. For example, the computing device 500 may be a conventional standalone computer or alternatively, the functions of computing device 500 may be distributed across multiple computer systems and architectures. In FIG. 5, the computing device 500 is linked, via network or local network, to other servers or systems.

The computing device 500 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 578 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 576 comprises a processor, such as one or more conventional microprocessors and one or more supplementary co-processors such as math co-processors for offloading workload from the CPU 576. The CPU 576 is in communication with the communications interface unit 578 and the input/output controller 580, through which the CPU 576 communicates with other devices such as other servers, user terminals, or devices. The communications interface unit 578 and the input/output controller 580 may include multiple communication channels for simultaneous communication with, for example, other processors, servers or client terminals.

The CPU 576 is also in communication with the data storage device. The data storage device may comprise an appropriate combination of magnetic, optical or semiconductor memory, and may include, for example, RAM 572, ROM 574, flash drive, an optical disc such as a compact disc or a hard disk or drive. The CPU 576 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 576 may be connected to the data storage device via the communications interface unit 578. The CPU 576 may be configured to perform one or more particular processing functions.

The data storage device may store, for example, (i) an operating system 582 for the computing device 500; (ii) one or more applications 584 (e.g., computer program code or a computer program product) adapted to direct the CPU 576 in accordance with the systems and methods described here, and particularly in accordance with the processes described in detail with regard to the CPU 576; or (iii) database(s) 586 adapted to store information that may be utilized to store information required by the program.

The operating system 582 and applications 584 may be stored, for example, in a compressed, an un-compiled and an encrypted format, and may include computer program code. The instructions of the program may be read into a main memory of the processor from a computer-readable medium other than the data storage device, such as from the ROM 574 or from the RAM 572. While execution of sequences of instructions in the program causes the CPU 576 to perform the process steps described herein, hard-wired circuitry may be used in place of, or in combination with, software instructions for implementation of the processes of the present invention. Thus, the systems and methods described are not limited to any specific combination of hardware and software.

Suitable computer program code may be provided for performing one or more functions in relation to the management of sepsis care as described herein. The program also may include program elements such as an operating system 582, a database management system and "device drivers" that allow the processor to interface with computer peripheral devices (e.g., a video display, a keyboard, a computer mouse, etc.) via the input/output controller 580.

The term "computer-readable medium" as used herein refers to any non-transitory medium that provides or participates in providing instructions to the processor of the computing device 500 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 576 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 500 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 6:
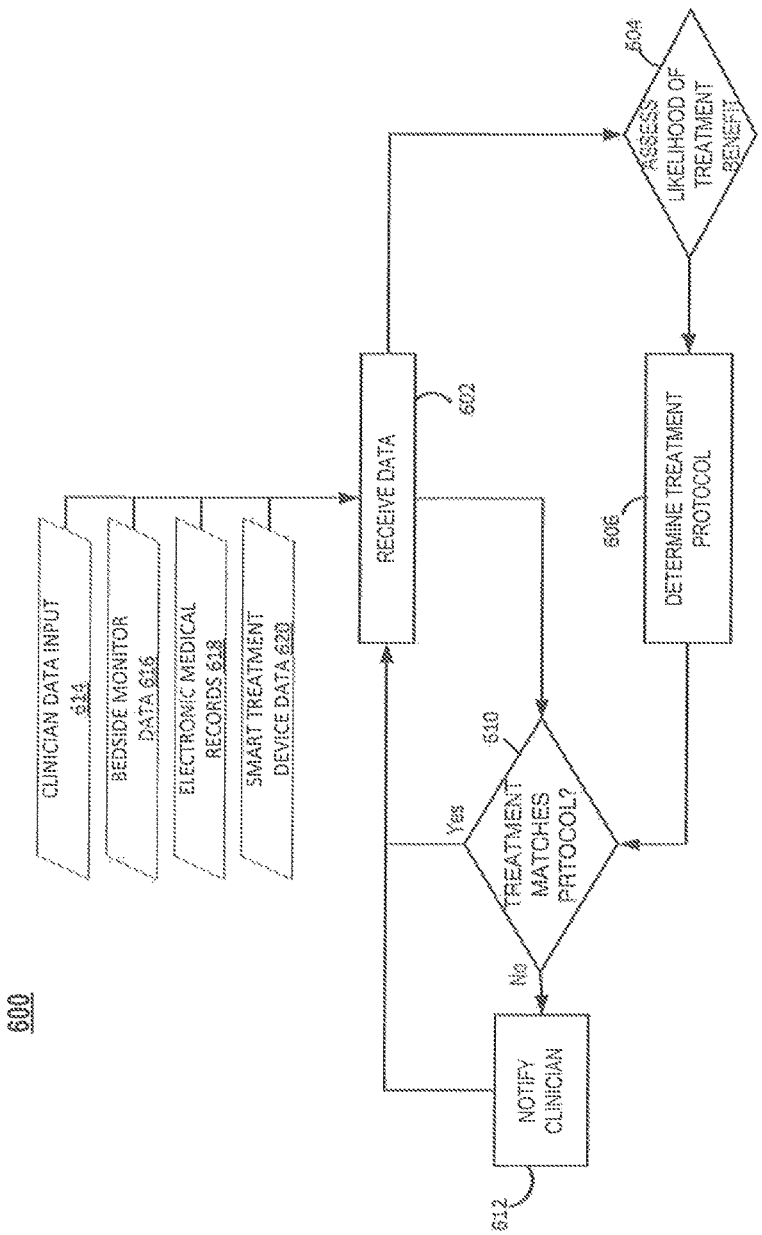
FIG. 6 is a flowchart that details a method for managing sepsis care, according to an illustrative embodiment.

FIG. 6 is a flowchart of a method 600 that may be implemented by the present disclosure to provide sepsis care management. In general, the method 600 analyzes data relating to a patient to determine both the patient's risk for sepsis and whether that risk is addressed appropriately and consequently. An overview of the method will first be provided, followed by illustrations of various implementations of the steps of the method. As shown, the method 600 includes receiving data (step 602). In some implementations, the data is received by data receiver 102 and communicated to risk and treatment model 104, which assesses the likelihood the patient would benefit from treatment (step 604) and determines either an appropriate treatment protocol (step 606). As the clinicians administer treatment, the data receiver 102 receives treatment data (step 602) and compares, using the compliance evaluator 106, the treatment data to the treatment protocol continuously until the compliance evaluator 106 detects a substantial difference (step 610) and notifies the clinician (step 612).

At step 602, the data receiver 102 aggregates data related to the patient. In an example, the data receiver 102 may interface with the patient's physiological monitors in order to receive real time physiological data, shown as the bedside monitor data 616, such as an EKG, respiration rate, blood pressure, oxygen saturation, or data from any device connected to a general purpose input. The data receiver 102 may alternatively or additionally interface with the hospital records system to retrieve patient data, shown as the electronic medical records 618, such as medical history, the patient's chief complaints, lab test results, and radiological data. To obtain treatment information beyond the medical records, step 602 includes receiving information from the treatment devices interface 238 (as the smart treatment device data 620) and/or information obtained through the clinician interface 224 (as the clinician data input 614). In some implementations, only a subset of the patient information is available and/or used for screening at any given time. At step 602, the data receiver 102 continuously monitors the patient and forwards the data for use in step 604 and step 610.

At step 604, the risk and treatment model 104 receives the patient data from the data receiver 102. In the exemplary implementation, the statistical model 350 receives as input the patient data (such as physiological data, physiological waveform data, treatment data, and medical records data, for example) and produces the likelihood indicator 352 (such as the computed probability that the patient would benefit from IV fluids). In some implementations, the likelihood indicator 352 is a scalar probability value. In other implementations, likelihood indicator 352 places the patient's benefit level into bins, such as very high, high, moderate, low, very low, none, or any suitable combination thereof, or provides a probability that the patient's status falls in any bin. In general, any number of bins may be used, where each bin represents a nuanced likelihood level. Since the statistical model 350 is user configurable, the output likelihood indicator 352 may be selected to be in a format that is suitable for input to the user configurable treatment protocol selector 354. If step 604 computes a low likelihood of benefit, the risk and treatment model 104 may not initiate a treatment protocol, stand down a previously suggested critical action, continue surveillance, or the risk and treatment model 104 may order at least one additional diagnostic test to provide additional data to steps 602 and 604 so that increasingly discriminatory models can be applied. In some implementations, the method 600 comprises notifying the clinician of the at least one additional diagnostic action to be conducted or simply of the low risk determination. In step 606, if step 604 calculated a likelihood of treatment benefit, the target treatment protocol selector selects target treatment protocol 112 from a plurality of candidate treatment protocols. In some implementations, the steps of the target treatment protocol 112 are displayed on the clinician interface 224. In other implementations, the notifications system 460 can alert the clinician to changes in the target treatment protocol 112. In some implementations, steps 604 is incorporated into step 606 of the method 600. For example, the assessment of the likelihood of benefiting from treatment of sepsis in step 604 may be implicitly performed at step 606 when the target treatment protocol 112 is determined by calculating the likelihood that each potential treatment will be beneficial.

At step 610, the compliance evaluator 106 receives the clinician action data 110 that was collected in step 602 and communicated by the data receiver 102. At step 610, the compliance evaluator 106 compares the clinician action data 110 to the target treatment protocol 112 to determine whether the prescribed clinical actions were undertaken at the appropriate times. If prescribed actions were not undertaken at the appropriate time, the method 600 proceeds to step 612 and compliance notification 114 is sent to indicate a lapse in care. In some implementations, the user may configure the compliance evaluator 106 to send notifications at multiple times for each action, such as messages at the beginning of the time duration for a treatment step or a warning some time before the end of the duration. Steps 610 and 612 both return to step 602 to continuously monitor the patient and treatment data.

Figure 7:
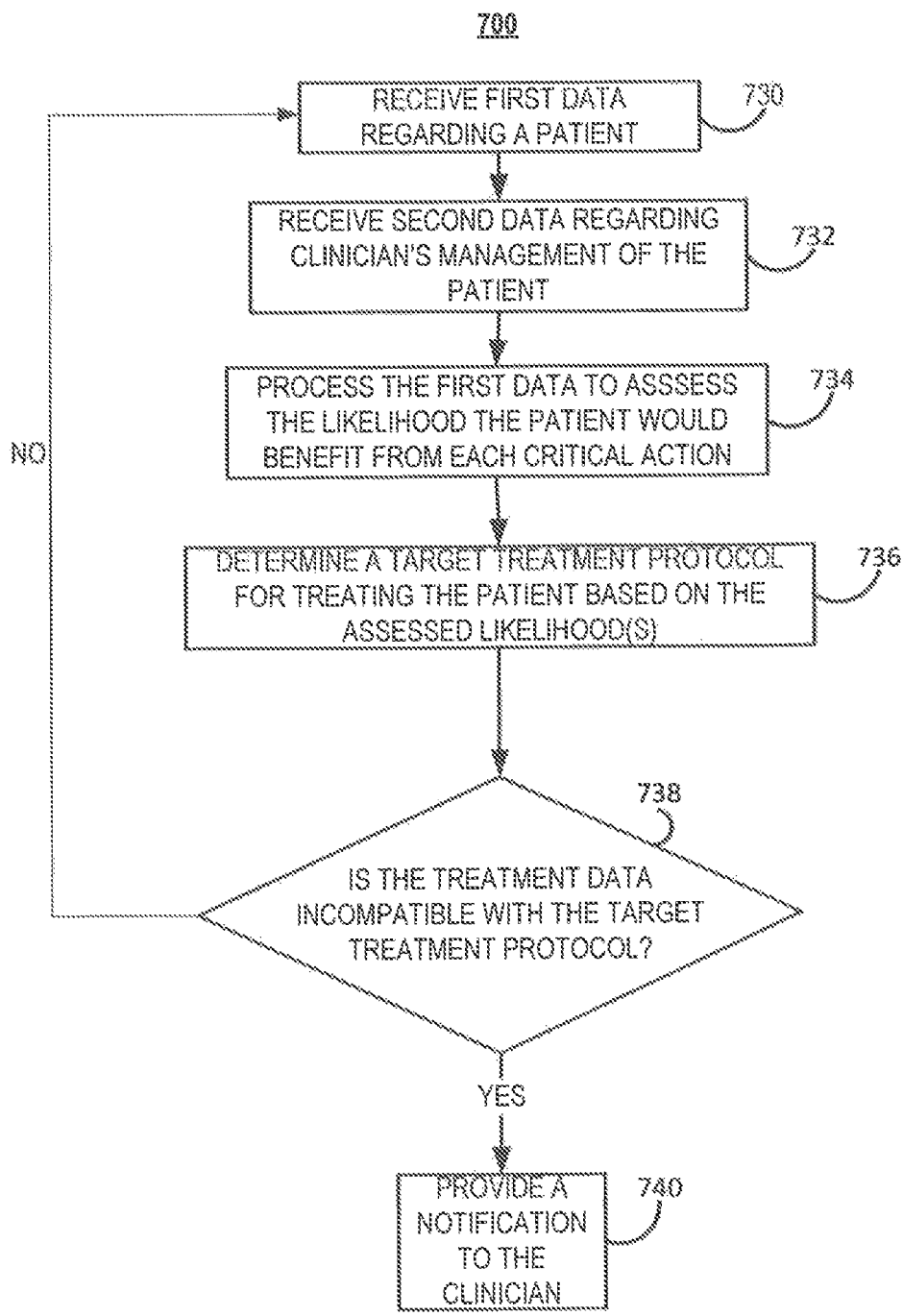
FIG. 7 is a flowchart that details a method for sepsis care management, according to an illustrative embodiment.

FIG. 7 is a flowchart of a method 700 that may be implemented by the present disclosure to provide sepsis care management. In general, the method 700 analyzes first data relating to a patient and second data relating to a clinician's management of the patient to determine both the likelihood that the patient would benefit from a critical action and whether beneficial critical actions are administered appropriately and consequently. As shown, the method 700 includes receiving first data regarding a patient (step 730). In some implementations, the data, which includes physiological measurements, past medical history variables, current complaint variables, and diagnostic data, is received by data receiver 102 and communicated to risk and treatment model 104, which applies a statistical probability model to assess the likelihood that the patient would benefit from each of the potential critical actions the clinician may employ to treat a potentially septic patient (step 734) and uses additional models to determine an appropriate target treatment protocol for treating the patient based on the assessed likelihoods (step 736). In some implementations, the likelihoods of benefiting from each treatment are computed with increasing certainty based on the potentially limited amounts of information available. Step 734 may advise that antibiotics should be initiated based on age and triage temperature but, once comprehensive diagnostic data is available, may also indicate that further antibiotics are of little benefit. As the clinicians administer treatment, the data receiver 102 receives second data regarding the clinician's treatment (step 732) and continuously compares, using the compliance evaluator 106, the treatment data to the treatment protocol. If the compliance evaluator 106 detects a substantial incompatibility (step 738), a compliance notification 114 is provided to the clinician (step 740).

At step 730, first data regarding a patient is received by data receiver 102. In some implementations the first data is received through physiological monitors interface 230, clinical records interface 236, or clinician interface 224 and is communicated to other elements of the present disclosure as patient data 108. This first data may relate to a patient's age, recorded physiological data, medical history, chief complaints, diagnostic test results, radiological data, and any other suitable patient related data.

At step 732, second data regarding a clinician's management of the patient is received by data receiver 102. In some implementations the second data is received through clinician interface 224, clinical records interface 236, and treatment devices interface 238 and is communicated to other elements of the present disclosure as clinician action data 110. This second data relates to the treatment the patient is receiving, such as the timings and details of critical actions administered by the clinician as communicated by smart treatment devices and interfaces, such as a measurement device that measures an amount of a fluid flowing into or out of the patient, a bar code scanner that scans a label of a medication that is administered to the patient, a touchscreen monitor that accepts as input data indicative of a medication that is administered to the patient, or any other suitable smart treatment device/interface.

At step 734, the first data is processed by the risk and treatment model 104 to assess a likelihood that the patient would benefit from administration of each of one or more critical actions for the treatment of potentially septic patients. One such critical action relates to a request for at least one additional diagnostic action that may be recommended by the risk and treatment model 104 in order to improve its diagnostic power. Diagnostic actions can include any action or test that is suitable for obtaining diagnostic data or information that may be used to diagnose a potentially septic patient. Examples of diagnostic actions include (a) specific diagnostic serum testing, (b) routine, continual monitoring (e.g., repeat blood pressure testing, BP, every 60 min), (c) enhanced monitoring (e.g., repeat BP immediately, or in 5 min, or every 15 min, or initiating an indwelling arterial catheter for continuous blood pressure monitoring), and (d) evaluating the patient's response to therapy (e.g., change in heart rate and blood pressure after receiving a 500 cc saline bolus intravenously). Critical actions can also include therapeutic actions, which include actions such as (a) administering one dose of broad spectrum antibiotics, (b) continual dosing of antibiotics (e.g., every 8 hours), (c) administering one bolus of saline intravenously, (d) continuous saline infusion (e.g., 200 cc/hour), and (e) the initiation of vasopressors. These examples are provided by way of illustration only, and one of ordinary skill in the art will understand that in general, any suitable diagnostic action or critical action may be used without departing from the scope of the present disclosure. Any critical action that the clinician may suitably employ to treat sepsis may be assigned a likelihood of being beneficial to the specific patient. After initial benefit calculations, the data receiver 102 will continue to receive patient data, and the likelihoods of benefit for each critical action will be updated based on the additional data. The risk and treatment model 104 may store previous likelihood results to compare against the updated likelihoods.

At step 736, a target treatment protocol for treating the patient based on the assessed likelihoods is determined by the risk and treatment model 104. The target treatment protocol includes a decision for each of the one or more critical actions, which may include diagnostic tests, antibiotics administration, fluid administration, vasopressor administration, or any suitable combination thereof. In some implementations, the decision is a binary decision whether the likelihood of benefit for each critical action exceeds a configurable threshold. When presented with an updated likelihood of benefit for a critical action, the treatment protocol selector 354 may determine that the updated value is significantly smaller than the previous value, for example if the updated value fails to reach the same threshold as the original value, and, consequently, may both cease to recommend a previously recommended critical action and notify the clinician of the change in the recommended target treatment protocol.

At step 738, the compliance evaluator 106 compares the second data to the target treatment protocol and provides a notification to the clinician if the second data is incompatible with the target treatment protocol. The compliance evaluator 106 receives clinician action data 110 that is indicative of the treatment actually being administered to the patient and compares the timings and details of the treatment to the target treatment protocol as well as orders that have been recently removed from the target treatment protocol and remain stored in the compliance evaluator 106. If an administration deadline in the protocol is missed, a treatment that has been stood down is continuously administered, or the details of the treatment, such as a dosage, are different from the protocol by more than a configurable threshold amount, then notification system 460 can provide a notification to the system that the administered treatment is incompatible with the prescribed target treatment protocol.

Sepsis is a dangerous and common medical emergency with an insidious onset and, once severe sepsis has developed, a very high mortality rate. Yet despite this staggeringly high mortality, sepsis care is often idiosyncratic and vulnerable to lapses in treatment. Mild infections are exceedingly common, but, in theory, if aggressive treatment were to be initiated and consequently administered when the infection was in its earlier, milder state, then sepsis and critical illness could be either avoided altogether, or at least mitigated. Yet, there is currently no single test or clinical finding that clearly defines the progression of infection and the development of a severe, life-threatening septic state. The usual assumption is that once a doctor writes the orders for treatment initiation, the orders will be followed consequently and expeditiously, and that staff will also routinely re-assess patients after various interventions, to evaluate treatment efficacy and, when necessary, provide subsequent interventions. Yet in practice, while the patient's condition evolves through time, management may lag, ranging from delayed enactment of initial orders to delayed re-evaluation and delayed ordering of subsequent treatments.

Described herein are sepsis care management systems and methods that integrate available data relating to the patient and the treatment they are receiving to prescribe and enforce standardized sepsis treatment protocols that are continuously monitored and re-evaluated as the patient's condition evolves. The risk and treatment model 104 has the ability to screen patients with minimal physiological input and give a quantitative assessment of the patient's likelihood of benefiting from sepsis treatment. This provides a substantial benefit in a clinical setting, as this screening allows for standardized levels of precautionary treatment to fight the infection in its more mild stage before diagnostic data can be obtained. The data receiver 102 also monitors the treatment that is administered to the patient. This monitoring, such as from smart treatment devices, allows for a precise, continuous treatment record that can be used in real time to inform further treatments, to determine if treatment has been initiated, and to determine if that treatment adheres to a clinical sepsis treatment protocol.

It is to be understood that while various illustrative implementations have been described, the forgoing description is merely illustrative and does not limit the scope of the invention. While several examples have been provided in the present disclosure, it should be understood that the disclosed systems, components and methods of manufacture may be embodied in many other specific forms without departing from the scope of the present disclosure.

The examples disclosed can be implemented in sub-combinations with one or more other features described herein. A variety of apparatus, systems and methods may be implemented based on the disclosure and still fall within the scope of the invention. Also, the various features described or illustrated above may be combined or integrated in other systems or certain features may be omitted, or not implemented.

Examples of changes, substitutions, and alterations are ascertainable by one skilled in the art and could be made without departing from the scope of the information disclosed herein. Certain particular aspects, advantages, and modifications are within the scope of the following example implementations. All references cited herein are incorporated by reference in their entirety and made part of this application.

What is claimed is:

1. A method for sepsis care management, the method comprising:
  receiving, by at least one processor, first data regarding a patient and second data regarding a clinician's management of the patient, wherein the first data is received at a first time;

processing the first data to assess, for each of a plurality of critical actions for treatment of sepsis, a first likelihood that the patient would benefit from administration of the critical action, wherein at least one of the plurality of critical actions relates to a request for at least one additional diagnostic action;

subsequent to the processing of the first data to assess the first likelihoods, determining a target treatment protocol for treating the patient based on the assessed likelihoods using a target treatment protocol selector, the target treatment protocol selector being configured to determine the target treatment protocol based, at least in part, on a plurality of user-configurable thresholds, each of which corresponds to one of the plurality of critical actions, wherein determining the target treatment protocol is performed, at least in part, by comparing the assessed first likelihood for each critical action to the corresponding user-configurable threshold for that critical action, wherein determining the target treatment protocol is further based, at least in part, on local patient population information, wherein the target treatment protocol comprises a decision for each of the plurality of critical actions;

comparing the second data to the target treatment protocol;

providing a notification to the clinician if the second data is incompatible with the target treatment protocol;

receiving, at a second time later than the first time, additional first data regarding the patient;

processing the additional first data to assess updated likelihoods that the patient would benefit from administration of each of the plurality of critical actions for the treatment of sepsis; and;

determining an updated target treatment protocol for treating the patient based on the updated likelihoods.

2. The method of claim 1, wherein the notification is a first notification, the method further comprising providing a second notification to the clinician when at least one of the updated likelihoods is smaller than the corresponding first likelihood, the second notification indicating that at least one of the plurality of critical actions previously recommended in the target treatment protocol is not currently recommended in the updated target treatment protocol.

3. The method of claim 1, wherein the first data comprises at least one of an age of the patient, a medical history of the patient, a complaint of the patient, and physiological data recorded from the patient.

4. The method of claim 1, wherein the second data comprises data recorded by a plurality of devices that communicate information regarding treatment of the patient, and at least one device in the plurality of devices includes at least one of (1) a measurement device that measures an amount of a fluid flowing into or out of the patient, (2) a bar code scanner that scans a label of a medication that is administered to the patient, and (3) a touchscreen monitor that accepts as input data indicative of a medication that is administered to the patient.

5. The method of claim 1, wherein processing the first data to assess the likelihoods comprises providing the first data as input to a statistical probability model trained to compute the likelihoods that the patient would benefit from administration of the plurality of critical actions, wherein the likelihoods are computed specifically for the patient.

6. The method of claim 5, wherein determining the target treatment protocol further comprises weighting at least one input parameter used in the statistical probability model based, at least in part, on the local patient population information.

7. The method of claim 1, wherein the user-configurable thresholds are different for the different critical actions.

8. The method of claim 1, wherein determining the target treatment protocol further comprises selecting a set of binary decisions, each binary decision corresponding to one of the plurality of critical actions, wherein the binary decision for each respective critical action is based on whether the respective likelihood exceeds the respective user-configurable threshold, wherein the target treatment protocol corresponds to the set of binary decisions.

9. The method of claim 8, wherein each candidate treatment protocol in a plurality of candidate treatment protocols comprises a set of binary decisions related to the one or more critical actions, and wherein at least one of the critical actions is related to at least one of the group consisting of diagnostic tests, antibiotics administration, fluid administration, and vasopressor administration.

10. The method of claim 1, further comprising determining whether the second data is incompatible with the target treatment protocol by:
evaluating a discrepancy between the target treatment protocol and the second data; and
determining that the discrepancy exceeds a predetermined threshold.

11. The method of claim 1, wherein processing the first data to assess the likelihood for a first critical action of the plurality of critical actions is performed based, at least in part, on the assessed likelihood for a second critical action of the plurality of critical actions.

12. The method of claim 1, wherein one or more of the likelihoods is a scalar probability value.

13. The method of claim 1, wherein processing the first data to assess the likelihoods comprises determining whether one or more of the likelihoods falls within one of a plurality of bins, each of which represents a different likelihood level.

14. The method of claim 1, wherein determining the target treatment protocol further comprises determining the target treatment protocol based at least in part on patient data.

15. The method of claim 14, wherein the patient data is the first data.

16. The method of claim 1, wherein the target treatment protocol selector is configured to determine the target treatment protocol based, at least in part, on configurable clinical rules selected by the user.

17. A system for sepsis care management, the system comprising:
at least one input port configured to receive (1) first data regarding a patient and (2) second data regarding a clinician's management of the patient, wherein the first data is received at a first time, and wherein the at least one input port is further configured to receive, at a second time later than the first time, additional first data regarding the patient;
at least one processor that is in communication with the at least one input port and is configured to:
process the first data to assess, for each of a plurality of critical actions for treatment of sepsis, a first likelihood that the patient would benefit from administration of the critical action, wherein at least one of the plurality of critical actions relates to a request for at least one additional diagnostic action;
determine, subsequent to the process step, a target treatment protocol for treating the patient based on the assessed first likelihoods using a target treatment protocol selector, the target treatment protocol selector being configured to determine the target treatment protocol based, at least in part, on a plurality of user-configurable thresholds, each of which corresponds to one of the plurality of critical actions, wherein determining the target treatment protocol is performed, at least in part, by comparing the assessed first likelihood for each critical action to the corresponding user-configurable threshold for that critical action, wherein determining the target treatment protocol is further based, at least in part, on local patient population information, wherein the target treatment protocol comprises a decision for each of the plurality of critical actions;
compare the second data to the target treatment protocol;
process the additional first data to assess updated likelihoods that the patient would benefit from administration of each of the plurality of critical actions for the treatment of sepsis; and
determine an updated target treatment protocol for treating the patient based on the updated likelihoods; and
an output port configured to provide a notification to the clinician if the second data is incompatible with the target treatment protocol.

18. The system of claim 17, wherein the notification is a first notification, and the output port is further configured to provide a second notification to the clinician when at least one of the updated likelihoods is smaller than the corresponding first likelihood, the second notification indicating that at least one of the plurality of critical actions previously recommended in the target treatment protocol is not currently recommended in the updated target treatment protocol.

19. The system of claim 17, wherein the first data comprises at least one of an age of the patient, a medical history of the patient, a complaint of the patient, and physiological data recorded from the patient.

20. The system of claim 17, wherein the second data comprises data recorded by a plurality of devices that communicate information regarding treatment of the patient, and at least one device in the plurality of devices includes at least one of (1) a measurement device that measures an amount of a fluid flowing into or out of the patient, (2) a bar code scanner that scans a label of a medication that is administered to the patient, and (3) a touchscreen monitor that accepts as input data indicative of a medication that is administered to the patient.

21. The system of claim 17, wherein the at least one processor is configured to process the first data to assess the likelihoods by providing the first data as input to a statistical probability model trained to compute the likelihoods that the patient would benefit from administration of the plurality of critical actions, wherein the likelihoods are computed specifically for the patient.

22. The system of claim 21, wherein the at least one processor is configured to determine the target treatment protocol further comprises weighting at least one input parameter used in the statistical probability model based, at least in part, on the local patient population information.

23. The system of claim 17, wherein the user-configurable thresholds are different for the different critical actions.

24. The system of claim 17, wherein the at least one processor is configured to determine the target treatment protocol by selecting a set of binary decisions, each binary decision corresponding to one of the plurality of critical actions, wherein the binary decision for each respective critical action is based on whether the respective likelihood exceeds the respective user-configurable threshold, wherein the target treatment protocol corresponds to the set of binary decisions.

25. The system of claim 24, wherein each candidate treatment protocol in a plurality of candidate treatment protocols comprises a set of binary decisions related to the one or more critical actions, and wherein at least one of the critical actions is related to at least one of the group consisting of diagnostic tests, antibiotics administration, fluid administration, and vasopressor administration.

26. The system of claim 17, wherein the processor is further configured to determine whether the second data is incompatible with the target treatment protocol by:
evaluating a discrepancy between the target treatment protocol and the second data; and
determining that the discrepancy exceeds a predetermined threshold.

27. The system of claim 17, wherein the at least one processor is configured to process the first data to assess the likelihood for a first critical action of the plurality of critical actions based, at least in part, on the assessed likelihood for a second critical action of the plurality of critical actions.

28. The system of claim 17, wherein one or more of the likelihoods is a scalar probability value.

29. The system of claim 17, wherein the process step comprises determining whether one or more of the likelihoods falls within one of a plurality of bins, each of which represents a different likelihood level.

30. The system of claim 17, wherein the at least one processor is configured to determine the target treatment protocol by determining the target treatment protocol based at least in part on patient data.

31. The system of claim 30, wherein the patient data is the first data.

32. The system of claim 17, wherein the target treatment protocol selector is configured to determine the target treatment protocol based, at least in part, on configurable clinical rules selected by the user.

33. A method of treating a potentially septic patient, comprising:
performing at least one action selected from the group consisting of:
performing a diagnostic test;
administering an antibiotic;
administering a fluid; and
administering a vasopressor;
wherein the performing of the at least one action is based, at least in part, on:
receiving, by at least one processor, first data regarding a patient and second data regarding a clinician's management of the patient, wherein the first data is received at a first time;
processing the first data to assess first likelihoods, for each of a plurality of critical actions, that the patient would benefit from administration of the critical action, wherein at least one of the plurality of critical actions relates to a request for at least one additional diagnostic action; and
determining a target treatment protocol for treating the patient based on the assessed first likelihoods using a target treatment protocol selector, the target treatment protocol selector being configured to determine the target treatment protocol based, at least in part, on a plurality of user-configurable thresholds, each of which corresponds to one of the plurality of critical actions, wherein determining the target treatment protocol is performed, at least in part, by comparing the assessed first likelihood for each critical action to the corresponding user-configurable threshold for that critical action, wherein determining the target treatment protocol is further based, at least in part, on local patient population information, wherein the target treatment protocol comprises a decision for each of the plurality of critical actions;

receiving, at a second time later than the first time, additional first data regarding the patient;

processing the additional first data to assess updated likelihoods that the patient would benefit from administration of each of the plurality of critical actions for the treatment of sepsis; and determining an updated target treatment protocol for treating the patient based on the updated likelihoods.

\* \* \* \* \*